United States Patent
Sato et al.

(10) Patent No.: US 10,633,391 B2
(45) Date of Patent: Apr. 28, 2020

(54) DIOL, METHOD FOR MANUFACTURING DIOL, DI(METH)ACRYLATE, AND METHOD FOR MANUFACTURING DI(METH)ACRYLATE

(71) Applicant: MITSUBISHI GAS CHEMICAL COMPANY, INC., Chiyoda-ku (JP)

(72) Inventors: Hideyuki Sato, Niigata (JP); Atsushi Okamoto, Niigata (JP); Taketo Ikeno, Niigata (JP); Tetsuya Shimo, Niigata (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 0 days.

(21) Appl. No.: 16/342,329

(22) PCT Filed: Oct. 11, 2017

(86) PCT No.: PCT/JP2017/036844
§ 371 (c)(1),
(2) Date: Apr. 16, 2019

(87) PCT Pub. No.: WO2018/074305
PCT Pub. Date: Apr. 26, 2018

(65) Prior Publication Data
US 2019/0256524 A1    Aug. 22, 2019

(30) Foreign Application Priority Data
Oct. 18, 2016 (JP) .................. 2016-204125

(51) Int. Cl.
C07D 493/10    (2006.01)
C07B 61/00     (2006.01)

(52) U.S. Cl.
CPC ............ *C07D 493/10* (2013.01); *C07B 61/00* (2013.01)

(58) Field of Classification Search
CPC .................................................. C07D 493/10
USPC ................................................ 549/333, 335
See application file for complete search history.

(56) References Cited

U.S. PATENT DOCUMENTS

| | | |
|---|---|---|
| 2006/0057494 A1 | 3/2006 | Lee et al. |
| 2017/0240495 A1 | 8/2017 | Okamoto et al. |

FOREIGN PATENT DOCUMENTS

| | | |
|---|---|---|
| CN | 102020627 A | 4/2011 |
| EP | 3 211 013 A1 | 8/2017 |
| JP | 59-148776 A | 8/1984 |
| JP | 60-72883 A | 4/1985 |
| JP | 63-268722 A | 11/1988 |
| JP | 2000-44570 A | 2/2000 |
| JP | 2005-29563 A | 2/2005 |
| JP | 2006-83172 A | 3/2006 |
| JP | 2008-297327 A | 12/2006 |
| WO | WO 2016/052476 A1 | 4/2016 |

OTHER PUBLICATIONS

Aldrich, Handbook,1998-1999, p. 1681 and 1195, a 3 pages. (Year: 1998).*
International Search Report dated Dec. 19, 2017 in PCT/JP2017/036844 (submitting English translation only), 2 pages.
International Preliminary Report on Patentability and Written Opinion dated Dec. 19, 2017 in PCT/JP2017/036844 (with English translation), 11 pages.
Extended European Search Report dated Jul. 19, 2019 in Patent Application No. 17863267.5, 7 pages.

* cited by examiner

*Primary Examiner* — Taylor V Oh
(74) *Attorney, Agent, or Firm* — Oblon, McClelland, Maier & Neustadt, L.L.P.

(57) ABSTRACT

Provided is a diol that excels in thermal stability; and, a method for manufacturing a diol, a di(meth)acrylate, and a method for manufacturing a di(meth)acrylate. The diol represented by the formula (1) below; wherein each of $R^1$ and $R^2$ independently represents a hydrocarbon group; and each $R^3$ independently represents a hydrogen atom, hetero atom-containing group, halogen atom, straight chain alkyl group having 1 to 6 carbon atoms, branched alkyl group having 3 to 6 carbon atoms or, aryl group-containing group having 6 to 12 carbon atoms.

(1)

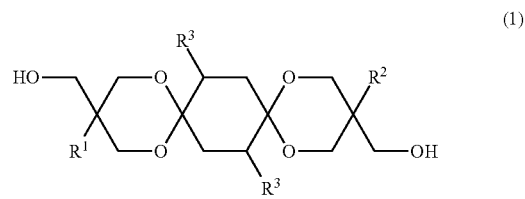

25 Claims, No Drawings

DIOL, METHOD FOR MANUFACTURING DIOL, DI(METH)ACRYLATE, AND METHOD FOR MANUFACTURING DI(METH)ACRYLATE

TECHNICAL FIELD

This invention relates to a diol that has a dispiro structure, and a method for manufacturing a diol; and, a di(meth)acrylate using a diol, and a method for manufacturing a di(meth)acrylate.

BACKGROUND ART

Since some years ago, spiroglycol (3,9-bis(2-hydroxy-1,1-dimethylethyl)-2,4,8,10-tetraoxaspiro[5.5]undecane) has been investigated. For example, Patent Literatures 1 to 3 disclose methods for manufacturing polyhydric alcohols having cyclic acetals, such as spiroglycol, intended for manufacturing high-purity polyhydric alcohols having cyclic acetals.

CITATION LIST

Patent Literature

[Patent Literature 1] JP-A-S59-148776
[Patent Literature 2] JP-A-2000-44570
[Patent Literature 3] JP-A-2005-29563

SUMMARY OF THE INVENTION

Technical Problem

Although the spiroglycol disclosed in Patent Literatures 1 to 3 are excellent materials, higher levels of thermal stability have been required in recent years.

This invention is aimed to solve the problem, and to provide a diol that excels in thermal stability; and, a method for manufacturing a diol, a di(meth)acrylate, and a method for manufacturing a di(meth)acrylate.

Solution to Problem

Considering the problem, the present inventors went through investigations, and found that a diol represented by the formula (1) below can solve the problem. More specifically, the aforementioned problem was solved by the means <1> below, and more preferably by the means <2> to <26> below.

<1> A diol represented by the formula (1) below:

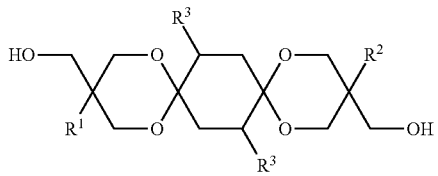

(1)

wherein each of $R^1$ and $R^2$ independently represents a hydrocarbon group; and each $R^3$ independently represents a hydrogen atom, hetero atom-containing group, halogen atom, straight chain alkyl group having 1 to 6 carbon atoms, branched alkyl group having 3 to 6 carbon atoms or, aryl group-containing group having 6 to 12 carbon atoms.

<2> The diol of <1>, wherein each $R^3$ in the formula (1) independently represents a hydrogen atom, straight chain alkyl group having 1 to 6 carbon atoms or branched alkyl group having 3 to 6 carbon atoms or, aryl group-containing group having 6 to 12 carbon atoms.

<3> The diol of <1>, wherein each $R^3$ in the formula (1) independently represents a hydrogen atom or methyl group.

<4> The diol of any one of <1> to <3>, wherein each of $R^1$ and $R^2$ in the formula (1) independently represents a straight chain alkyl group having 1 to 7 carbon atoms, branched alkyl group having 3 to 7 carbon atoms or aryl group.

<5> The diol of any one of <1> to <3>, wherein each of $R^1$ and $R^2$ in the formula (1) independently represents a straight chain alkyl group having 1 to 7 carbon atoms or, branched alkyl group having 3 to 7 carbon atoms.

<6> The diol of any one of <1> to <3>, wherein each of $R^1$ and $R^2$ in the formula (1) independently represents a straight chain alkyl group having 1 to 7 carbon atoms or aryl group.

<7> The diol of <1>, wherein each of $R^1$ and $R^2$ in the formula (1) independently represents an ethyl group, methyl group or phenyl group, and each $R^3$ represents a hydrogen atom.

<8> A method for manufacturing a diol, the method comprising allowing a 1,4-cyclohexanedione derivative represented by the formula (2) below, and a triol represented by the formula (3) below to undergo a dehydration cyclization reaction:

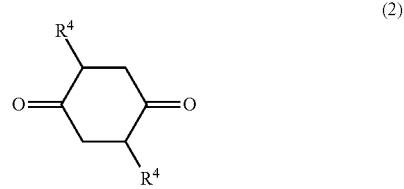

(2)

wherein each $R^4$ represents a hydrogen atom, hetero atom-containing group, halogen atom, straight chain alkyl group having 1 to 6 carbon atoms, branched alkyl group having 3 to 6 carbon atoms or, aryl group-containing group having 6 to 12 carbon atoms:

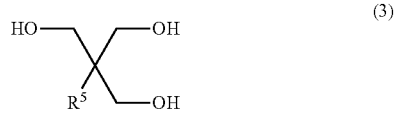

(3)

wherein $R^5$ represents a hydrocarbon group.

<9> The method for manufacturing a diol of <8>, wherein, in the formula (3), $R^5$ represents a straight chain alkyl group having 1 to 7 carbon atoms, branched alkyl group having 3 to 7 carbon atoms or aryl group.

<10> The method for manufacturing a diol of <8>, wherein, in the formula (3), $R^5$ represents a straight chain alkyl group having 1 to 7 carbon atoms or branched alkyl group having 3 to 7 carbon atoms.

<11> The method for manufacturing a diol of any one of <8> to <10>, wherein the dehydration cyclization reaction is allowed to proceed in the presence of an acid catalyst.

<12> The method for manufacturing a diol of <11>, wherein the acid catalyst contains at least one of methanesulfonic acid or para-toluenesulfonic acid.
<13> The method for manufacturing a diol of any one of <8> to <12>, the method comprising removing water resulted from the dehydration cyclization reaction, out from the reaction system.
<14> The method for manufacturing a diol of <13>, wherein the water resulted from the dehydration cyclization reaction is removed azeotropically with an organic solvent.
<15> The method for manufacturing a diol of <14>, wherein the organic solvent contains at least one of toluene or cyclohexane.
<16> The method for manufacturing a diol of any one of <8> to <15>, wherein the compound represented by the formula (2) is 1,4-cyclohexanedione, and the compound represented by the formula (3) is at least one of trimethylolpropane, trimethylolethane and tris(hydroxymethyl)toluene.
<17> The method for manufacturing a diol of any one of <8> to <15>, wherein the compound represented by the formula (2) is 1,4-cyclohexanedione, and the compound represented by the formula (3) is at least one of trimethylolpropane and trimethylolethane.
<18> The method for manufacturing a diol of any one of <8> to <17>, wherein the diol is the diol described in any one of <1> to <7>.
<19> A di(meth)acrylate represented by the formula (4) below:

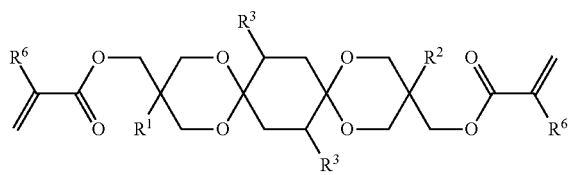

(4)

wherein each of $R^1$ and $R^2$ independently represents a hydrocarbon group, each $R^3$ independently represents a hydrogen atom, hetero atom-containing group, halogen atom, straight chain alkyl group having 1 to 6 carbon atoms, branched alkyl group having 3 to 6 carbon atoms or, aryl group-containing group having 6 to 12 carbon atoms, and each $R^6$ independently represents a hydrogen atom or methyl group.
<20> The di(meth)acrylate of <19>, wherein each $R^3$ in the formula (4) independently represents a hydrogen atom, straight chain alkyl group having 1 to 6 carbon atoms, branched alkyl group having 3 to 6 carbon atoms or, aryl group-containing group having 6 to 12 carbon atoms.
<21> The di(meth)acrylate of <19>, wherein each $R^3$ in the formula (4) independently represents a hydrogen atom or methyl group.
<22> The di(meth)acrylate of any one of <19> to <21>, wherein each of $R^1$ and $R^2$ in the formula (4) independently represents a straight chain alkyl group having 1 to 7 carbon atoms, branched alkyl group having 3 to 7 carbon atoms or aryl group.
<23> The di(meth)acrylate of any one of <19> to <21>, wherein each of $R^1$ and $R^2$ in the formula (4) independently represents a straight chain alkyl group having 1 to 7 carbon atoms or branched alkyl group having 3 to 7 carbon atoms.
<24> The di(meth)acrylate of any one of <19> to <21>, wherein each of $R^1$ and $R^2$ in the formula (4) independently represents a straight chain alkyl group having 1 to 7 carbon atoms or aryl group.
<25> The di(meth)acrylate of any one of <19> to <21>, wherein each of $R^1$ and $R^2$ in the formula (4) independently represents an ethyl group, methyl group or phenyl group; and each $R^3$ represents a hydrogen atom.
<26> A method for manufacturing a di(meth)acrylate, the method comprising allowing the diol described in any one of <1> to <7>, and (meth)acrylic acid to undergo a dehydration condensation reaction.

Advantageous Effects of Invention

With this invention, it now became possible to provide a diol that excels in thermal stability; and, a method for manufacturing a diol, a di(meth)acrylate, and a method for manufacturing a di(meth)acrylate.

DESCRIPTION OF EMBODIMENTS

This invention will further be detailed below. Note that, in this specification, all numerical ranges given by "to" with preceding and succeeding numerals mean to contain both numerals respectively as the lower limit value and the upper limit value.

(Meth)acrylate covers both of acrylate and methacrylate. The same will apply to (meth)acrylic acid and so forth.

Embodiments for carrying out this invention (simply referred to as "the embodiment(s)", hereinafter) will be detailed below. Note that the embodiments below are merely illustrative ones for explaining this invention, so that this invention is not solely limited to the embodiments.

The diol of the embodiment is specified by a diol represented by the formula (1) below:

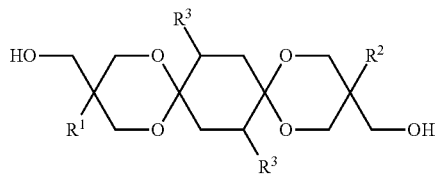

(1)

in the formula (1), each of $R^1$ and $R^2$ independently represents a hydrocarbon group; and each $R^3$ independently represents a hydrogen atom, hetero atom-containing group, halogen atom, straight chain alkyl group having 1 to 6 carbon atoms, branched alkyl group having 3 to 6 carbon atoms or, aryl group-containing group having 6 to 12 carbon atoms.

With such structure, the obtainable diol will have excellent thermal stability. In most cases, the diol represented by the formula (1) tends to show melting point lower than that of spiroglycol, and is therefore easier to handle. In addition with the structure represented by the formula (1), a rigid material will be obtained.

The diol represented by the formula (1) in the embodiment may typically have a melting point of 220° C. or below, which further may be 218° C. or below, 200° C. or below, or 180° C. or below. Although the lower limit value of melting point of the diol represented by the formula (1) is not specifically limited, the diol may be handled easily enough if the melting point is 150° C. or above, and even 160° C. or above.

The diol of the embodiment, represented by the formula (1) has a neo-structure, in which each β-position of two hydroxy groups has no hydrogen atom, and is therefore advantageous in that the diol is intrinsically less likely to produce olefins due to β-elimination.

The diol represented by the formula (1) may contain a plurality of geometrical isomers attributable to the acetal structure in the form of two six-membered rings. In the embodiment, any one of the geometrical isomers, or mixtures of two or more geometrical isomers will be shown. Also each of triply-arrayed, six-membered ring structures is left unfixed regarding the conformation, and is allowed to have any possible conformation. Ratio of generation of the geometrical isomers of the diol represented by the formula (1) varies depending on reaction conditions (types of reaction solvents, types of reaction catalyst, reaction temperature) and so forth, and is not specifically limited. The mixtures of geometrical isomers of diol, having the dispiro structure and obtainable in the embodiment, may be used in the form of such mixtures, or may be used after separating them into the individual geometrical isomers by any of known methods.

In the formula (1), $R^1$ and $R^2$ may be same or different, and represent a hydrocarbon group; preferably represent straight chain alkyl group having 1 to 7 carbon atoms, branched alkyl group having 3 to 7 carbon atoms or aryl group; more preferably represent straight chain alkyl group having 1 to 7 carbon atoms or branched alkyl group having 3 to 7 carbon atoms; and even more preferably represent straight chain alkyl group having 1 to 7 carbon atoms. Note, however, that hydrocarbon group represented by $R^1$ and $R^2$ contains no ether bond. In other possible embodiments, each of $R^1$ and $R^2$ independently represents straight chain alkyl group having 1 to 7 carbon atoms, branched alkyl group having 3 to 7 carbon atoms or aryl group.

The straight chain alkyl group having 1 to 7 carbon atoms is preferably straight chain alkyl group having 1 to 5 carbon atoms, more preferably straight chain alkyl group having 1 to 3 carbon atoms, and even more preferably methyl group or ethyl group.

The branched alkyl group having 3 to 7 carbon atoms is preferably branched alkyl group having 3 to 5 carbon atoms, more preferably branched alkyl group having 3 or 4 carbon atoms, and even more preferably branched alkyl group having three carbon atoms.

The aryl group is preferably aryl group having 6 to 20 carbon atoms, more preferably aryl group having 6 to 14 carbon atoms, even more preferably phenyl group, naphthyl group or anthracenyl group, and yet more preferably phenyl group.

Each of $R^1$ and $R^2$ in the formula (1) independently represents, for example, methyl group, ethyl group, n-propyl group, isopropyl group, n-butyl group, 1-methylpropyl group, 2-methylpropyl group, 1,1-dimethylethyl group (tert-butyl group), n-pentyl group, 1-methylbutyl group, 2-methylbutyl group, 3-methylbutyl group, 1-ethylpropyl group, 1,1-dimethylpropyl group, 1,2-dimethylpropyl group, 2,2-dimethylpropyl group (neopentyl group), n-hexyl group, 1-methylpentyl group, 2-methylpentyl group, 3-methylpentyl group, 4-methylpentyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group, 1-ethyl-2-methylpropyl group, n-heptyl group, 1-methylhexyl group, 2-methylhexyl group, 3-methylhexyl group, 4-methylhexyl group, 5-methylhexyl group, 1,1-dimethylpentyl group, 1,2-dimethylpentyl group, 1,3-dimethylpentyl group, 1,4-dimethylpentyl group, 1,5-dimethylpentyl group, 2,2-dimethylpentyl group, 2,3-dimethylpentyl group, 2,4-dimethylpentyl group, 3,3-dimethylpentyl group, 3,4-dimethylpentyl group, 4,4-dimethylpentyl group, 1-ethylpentyl group, 2-ethylpentyl group, 3-ethylpentyl group, 1-propylbutyl group, 2-propylbutyl group, 3-propylbutyl group, 1-ethyl-1-methylbutyl group, 1-ethyl-2-methylbutyl group, 1-ethyl-3-methylbutyl group, 2-ethyl-1-methylbutyl group, 2-ethyl-2-methylbutyl group, 2-ethyl-3-methylbutyl group, and 1,2,3-trimethylbutyl group, phenyl group, naphthyl group, and anthracenyl group.

Among them, each of $R^1$ and $R^2$ independently, and preferably represents a methyl group, ethyl group, n-propyl group, isopropyl group or n-butyl group, wherein methyl group or ethyl group is more preferable. Also preferable is an embodiment where at least one of $R^1$ or $R^2$ represents a phenyl group. From the viewpoint of particular simplicity of the manufacturing process, $R^1$ and $R^2$ are preferably identical. It is particularly preferable that $R^1$ and $R^2$ are identical, and represent methyl group or ethyl group. In still another embodiment, both of $R^1$ and $R^2$ preferably represent phenyl group.

In the formula (1), each $R^3$ independently represents a hydrogen atom, hetero atom-containing group, halogen atom, straight chain alkyl group having 1 to 6 carbon atoms, branched alkyl group having 3 to 6 carbon atoms or, aryl group-containing group having 6 to 12 carbon atoms; preferably represents a hydrogen atom, straight chain alkyl group having 1 to 6 carbon atoms, branched alkyl group having 3 to 6 carbon atoms or, aryl group-containing group having 6 to 12 carbon atoms; more preferably represents a hydrogen atom, straight chain alkyl group having 1 to 6 carbon atoms or branched alkyl group having 3 to 6 carbon atoms; even more preferably represents a hydrogen atom or methyl group; and yet more preferably represents a hydrogen atom.

The hetero atom contained in the hetero atom-containing group is exemplified by oxygen atom, sulfur atom, and nitrogen atom.

As preferred hetero atom-containing group, exemplified are alkoxy group, alkylthioether group, amino group and nitro group. The alkyl chain that composes the alkoxy group or alkylthioether group is preferably straight alkyl chain having 1 to 6 carbon atoms, and more preferably straight alkyl chain having 1 to 3 carbon atoms.

The straight chain alkyl group having 1 to 6 carbon atoms is preferably straight chain alkyl group having 1 to 5 carbon atoms, more preferably straight chain alkyl group having 1 to 3 carbon atoms, and even more preferably methyl group or ethyl group.

The branched alkyl group having 3 to 6 carbon atoms is preferably branched alkyl group having 3 to 5 carbon atoms, more preferably branched alkyl group having 3 or 4 carbon atoms, and even more preferably branched alkyl group having three carbon atoms.

The aryl group-containing group having 6 to 12 carbon atoms is preferably phenyl group, or alkyl group substituted with phenyl group. Phenyl group is more preferable. The alkyl group that composes the alkyl group substituted with phenyl group preferably has 1 to 3 carbon atoms, more preferably has 1 or 2 carbon atoms, and even more preferably one carbon atom.

$R^3$ in the formula (1) above is exemplified by, for example, hydrogen atom, methyl group, ethyl group, n-propyl group, isopropyl group, n-butyl group, 1-methylpropyl group, 2-methylpropyl group, 1,1-dimethylethyl group (tert-butyl group), n-pentyl group, 1-methylbutyl group, 2-methylbutyl group, 3-methylbutyl group, 1-ethylpropyl group, 1,1-dimethylpropyl group, 1,2-dimethylpropyl group, 2,2-dimethylpropyl group (neopentyl group), n-hexyl group, 1-methylpentyl group, 2-methylpentyl group, 3-methylpentyl group, 4-methylpentyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group, 1-ethyl-2-methylpropyl group, fluorine atom, chlorine atom, bromine atom, iodine atom, methoxy group, ethoxy group, propioxy group, butoxy group, methylthioether group, ethylthioether group, amino group, nitro group, phenyl group, and benzyl group.

Among them, $R^3$ more preferably represents a hydrogen atom, methyl group, ethyl group, n-propyl group, isopropyl group, or n-butyl group. From the viewpoint of industrial availability, particularly preferable is the case where $R^3$ represents a hydrogen atom.

As a preferred embodiment of the diol represented by the formula (1), exemplified is a diol in which each of $R^1$ and $R^2$ in the formula (1) independently represents an ethyl group, methyl group or phenyl group, and each $R^3$ represents a hydrogen atom. As other preferred embodiment of the diol represented by the formula (1), exemplified is a diol in which each of $R^1$ and $R^2$ in the formula (1) independently represents an ethyl group or methyl group, and each $R^3$ represents a hydrogen atom.

Diols preferably employed in the embodiment is shown below. Of course the embodiment is not limited thereto. Me stands for methyl group, Et for ethyl group, Pr for propyl group, and Bu for butyl group.

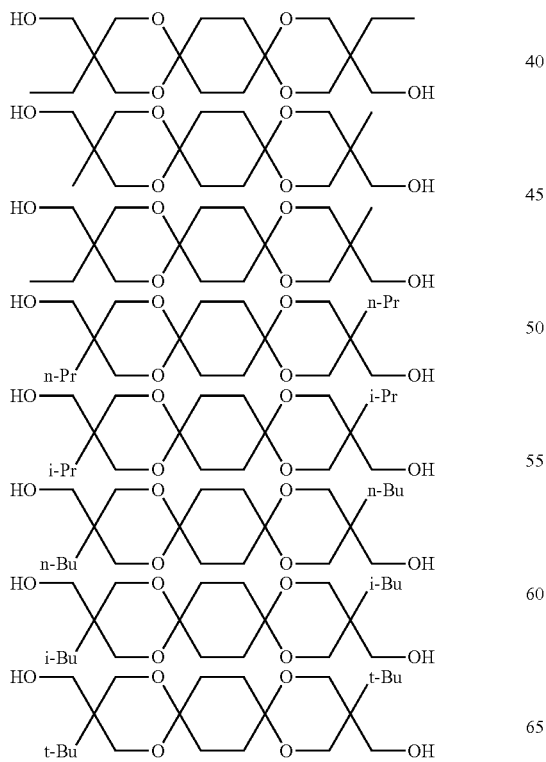

-continued

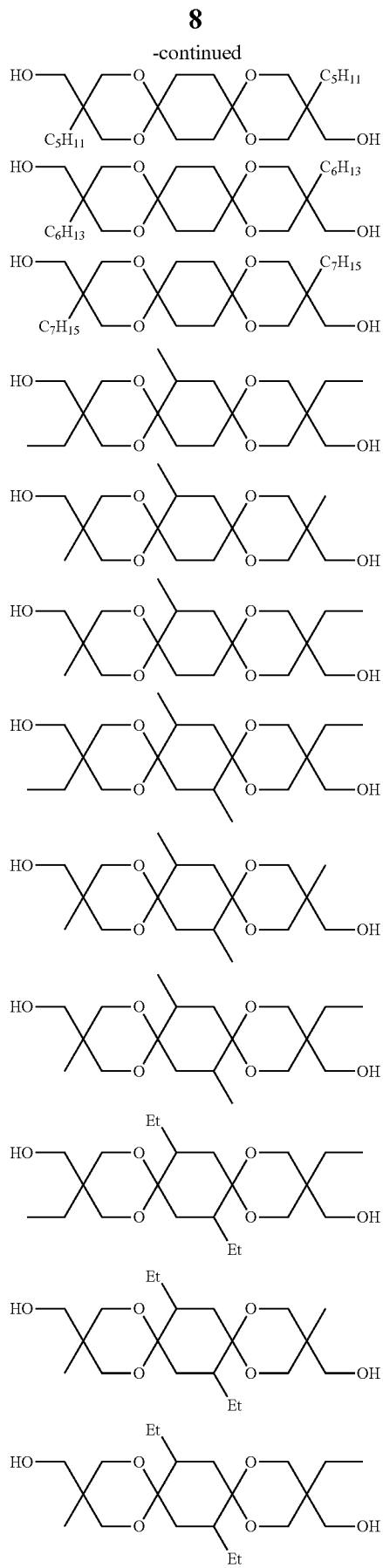

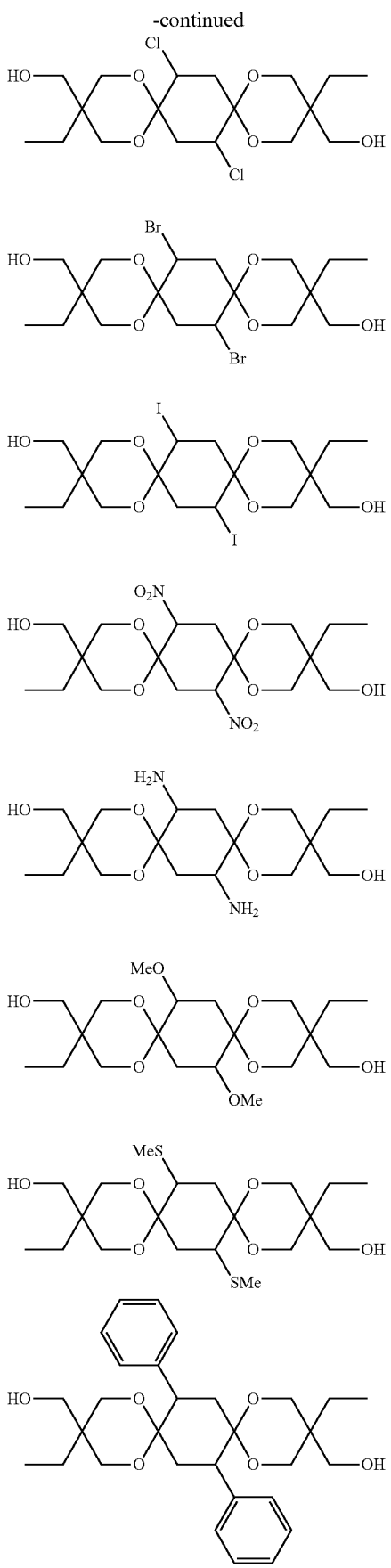

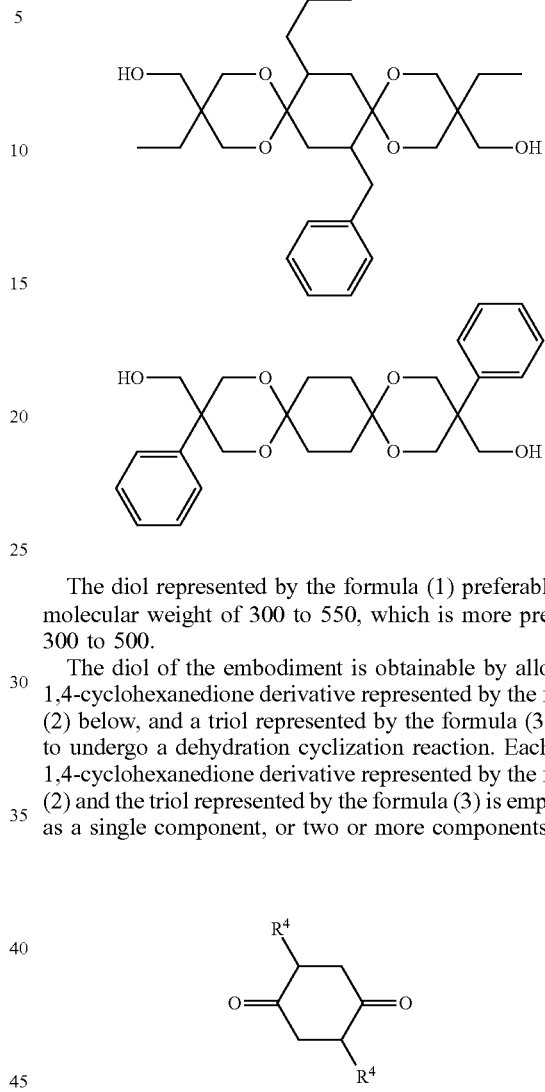

The diol represented by the formula (1) preferably has a molecular weight of 300 to 550, which is more preferably 300 to 500.

The diol of the embodiment is obtainable by allowing a 1,4-cyclohexanedione derivative represented by the formula (2) below, and a triol represented by the formula (3) below to undergo a dehydration cyclization reaction. Each of the 1,4-cyclohexanedione derivative represented by the formula (2) and the triol represented by the formula (3) is employable as a single component, or two or more components.

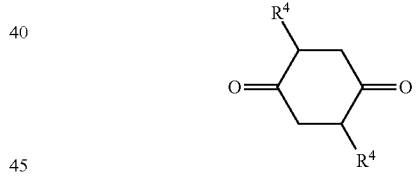
(2)

In the formula (2), each $R^4$ represents a hydrogen atom, hetero atom-containing group, halogen atom, straight chain alkyl group having 1 to 6 carbon atoms, branched alkyl group having 3 to 6 carbon atoms or, aryl group-containing group having 6 to 12 carbon atoms.

(3)

In the formula (3), $R^5$ represents a hydrocarbon group.

The hydrocarbon group refers to a straight chain alkyl group having 1 to 7 carbon atoms, branched alkyl group having 3 to 7 carbon atoms or aryl group. In one embodiment, $R^5$ represents a straight chain alkyl group having 1 to 7 carbon atoms or branched alkyl group having 3 to 7 carbon atoms. The hydrocarbon group represented by $R^5$, however, contains no ether bond.

R⁴ in the formula (2) is synonymous to R³ in the formula (1), along with the same preferred ranges.

The 1,4-cyclohexanedione derivative represented by the formula (2), used in the embodiment, is not specifically limited regarding methods of manufacturing, allowing use of the product manufactured by any of known methods. For example, *Organic Syntheses, Coll. Vol.* 5, p. 288 (1973); *Vol.* 45, p. 25 (1965) has reported a two-step method for synthesizing 1,4-cyclohexanedione from a succinic acid diester. *J. Chem. Soc., Perkin Trans.* 1, 1979, p3095 describes a method of synthesizing a 1,4-cyclohexanedione derivative having alkyl groups introduced to the α positions of carbonyl moieties. For easier usage, a marketed industrial product thereof may be used after purified, or may be used in its unpurified state.

The present inventors made a trial in the same way as in the embodiment, using cyclohexanedione isomers (1,2-form, 1,3-form), other than 1,4-cyclohexanedione. As a consequence, 1,2-dispiro form and 1,3-dispiro form were found to be produced, showing only a very low reaction yield. Since also a similar case has been described in paragraph [0021] of WO2016/052476, it is preferable to use the 1,4-cyclohexanedione derivative as the starting material for the diol having the dispiro structure of the embodiment, in pursuit of easier arrival to industrial high yield.

R⁵ in the formula (3) is synonymous to R¹ and R² in the formula (1), along with the same preferred ranges.

In the embodiment, particularly preferable is the case where the compound represented by the formula (2) is 1,4-cyclohexanedione, and the compound represented by the formula (3) is at least one of trimethylolpropane, trimethylolethane or tris(hydroxymethyl)toluene (preferably, at least one of trimethylolpropane or trimethylolethane).

In the dehydration cyclization reaction in the embodiment, the amount to be used of triol represented by the formula (3) above, relative to the amount to be used of the 1,4-cyclohexanedione derivative represented by the formula (2), is not specifically limited so long as the amount is enough for producing a desired diol having the dispiro structure. Since, however, the lesser the unreacted portion will be, the larger the industrial advantage will be, so that the ratio of the amount triol represented by the formula (3) relative to the amount to be used of 1,4-cyclohexanedione derivative represented by the formula (2), on the molar basis, is preferably 2.00 equivalent or above at the lowest, more preferably 2.05 equivalent or above, even more preferably 2.08 equivalent or above, and yet more preferably 2.10 equivalent or above. The amount to be used is preferably 5.00 equivalent or below at the highest, more preferably 3.00 equivalent or below, even more preferably 2.50 equivalent or below, and yet more preferably 2.30 equivalent or below.

The dehydration cyclization reaction (acetalizing reaction) in the embodiment is preferably allowed to proceed in the presence of an acid catalyst. Any known acid catalyst will suffice as the acid catalyst, without special limitation. Specific examples of employable acid catalyst include organic acids such as para-toluenesulfonic acid and methanesulfonic acid; mineral acids such as hydrochloric acid, sulfuric acid, nitric acid and phosphoric acid; and solid acid catalysts such as Nafion (from Sigma-Aldrich Inc., trade name) and cation exchange resin. Since the reaction product in the embodiment typically precipitates as a solid in the reaction liquid, so that the organic acids or mineral acids are preferably used from the viewpoint of simplicity of post-treatment after the reaction. In particular, the organic acids are preferably used as the acid catalyst in this invention. The acid catalyst is also preferably a homogeneous catalyst. The acid catalyst may also be a hydrate.

In this embodiment, the acid catalyst preferably contains at least one of methanesulfonic acid, para-toluenesulfonic acid, sulfuric acid, hydrochloric acid, nitric acid and phosphoric acid; more preferably contains at least one of methanesulfonic acid, para-toluenesulfonic acid and sulfuric acid; and even more preferably contains at least one of methanesulfonic acid and para-toluenesulfonic acid. Two or more types of acid catalysts may be used together.

The amount to be used of acid catalyst, although not specifically limited, is preferably 0.00001 to 0.1 equivalent, on the molar basis, relative to the amount of 1,4-cyclohexanedione derivative represented by the formula (2). From the viewpoint of reaction time, the amount is more preferably 0.00001 equivalent or more, and even more preferably 0.0001 equivalent or more. From the viewpoint of suppressing generation of by-products, and of removing the catalyst, the amount is more preferably 0.1 equivalent or less, and more preferably 0.05 equivalent or less.

In the dehydration cyclization reaction of the embodiment, an organic solvent may be used as the reaction solvent, besides the 1,4-cyclohexanedione derivative represented by the formula (2), the triol represented by the formula (3) and the acid catalyst. By using the organic solvent, it now becomes possible to easily remove water resulted from the dehydration cyclization reaction, out from the reaction system, and to thereby accelerate the dehydration cyclization reaction. Accordingly, the organic solvent is not specifically limited so long as it does not undergo side reaction with the starting materials. Preferably used are organic solvents which can stay separated from water phase, and can distill azeotropically with water. In this invention, not only the water resulted from the dehydration cyclization reaction, but also water inherent to the starting materials are preferably removed.

In other words, the method for manufacturing diol according to the embodiment preferably include a process of removal of water resulted from the dehydration cyclization reaction, out of the reaction system. Methods for removing water out from the reaction system are not specifically limited, allowing employment of any of known methods having been known as the methods for removing water resulted from dehydration reaction, out of the reaction system. In the embodiment, the water resulted from the dehydration cyclization reaction is preferably removed azeotropically with the organic solvent as described above, wherein the removal of water is preferably associated with removal water inherent to the starting materials.

For the azeotropic distillation with organic solvent, exemplified is a method by which the organic solvent and water are distilled off as an azeotropic fraction, and only the water phase of the liquid separated into two layers is removed from the system. Reaction temperature at which the water is removed, when using an organic solvent capable of forming an azeotrope with water, is not specifically limited, so long as the water and the organic solvent can distill azeotropically.

From the viewpoint of removing the water more easily from the reaction system, the organic solvent is preferably non-water-soluble or poorly water-soluble, and is more preferably a hydrocarbon solvent. The hydrocarbon solvent is preferably any of paraffins, aromatic hydrocarbons and alicyclic hydrocarbons; more preferably any of pentane, hexane, heptane, octane, benzene, toluene, xylene, cyclohexane, ligroin and petroleum ether; and even more preferably any of toluene and cyclohexane. Only one type of organic solvent may be used independently, or two or more types may be used in a mixed manner.

Now, "non-water-soluble or poorly water-soluble" refers to a property explained by a solubility to water of 2 g/L or below at room temperature.

The amount to be used of organic solvent, although not specifically limited, is preferably 10 to 10000 parts by mass, per 100 parts by mass in total of the 1,4-cyclohexanedione derivative represented by the formula (2) and the triol represented by the and formula (3), more preferably 20 to 5000 parts by mass, and even more preferably 30 to 1000 parts by mass. With the amount to be used of organic solvent thus controlled within the above described numerical ranges, the water may more effectively and thoroughly removed out from the system, when the organic solvent can form an azeotropic mixture together with water.

Reaction temperature of the dehydration cyclization reaction in the embodiment is typically 50 to 180° C., although depending on the boiling point of an organic solvent to be employed, which is preferably 70 to 150° C., and more preferably 85 to 125° C. If the reaction temperature is 50° C. or above, the reaction time will become shorter, meanwhile if the reaction temperature is 180° C. or below, coloration or the like, due to side reaction, will be suppressed. Reaction pressure of the dehydration cyclization reaction is not specifically limited, so long as the dehydration cyclization reaction can proceed at the aforementioned temperature, and may be normal pressure. In some cases, the reaction may even be allowed to proceed at a reduced pressure. Atmosphere around the reaction system during the reaction is not specifically limited, allowing choice from air atmosphere, nitrogen atmosphere, and nitrogen gas flow. Reaction time may properly be controlled depending on the amount of catalyst and the reaction temperature, which is preferably 2 to 48 hours in most cases, and more preferably 5 to 20 hours.

According to the method of the embodiment, the obtainable diol represented by the formula (1) may also have a purity of 95% by mass or above, when analyzed by GC (or by HPLC, if GC analysis is difficult). The obtainable diol represented by the formula (1) may also achieve an isolation yield of 90% by mass or above.

The diol obtainable by the method of the embodiment may be isolated by any of known methods of purification, after appropriately treated by neutralization, filtration, washing, condensation or the like. The methods are specifically exemplified by crystallization, distillation, adsorption, column chromatography, fractional HPLC (liquid chromatography), and fractional gas chromatography. Depending on purposes of the succeeding reaction, the diol may be used only after post-treatment in the manufacturing method of the embodiment, without being specially isolated.

The diol of the embodiment may be used as a starting material for various industrial materials. For example, the diol of the embodiment may be used as a starting material for thermoplastic resins and (meth)acrylates.

The (meth)acrylate may be monofunctional (meth)acrylate having a single (meth)acryloyloxy group, or may be di(meth)acrylate having two (meth)acryloyloxy groups.

The di(meth)acrylate of the embodiment is exemplified by a di(meth)acrylate represented by the formula (4) below:

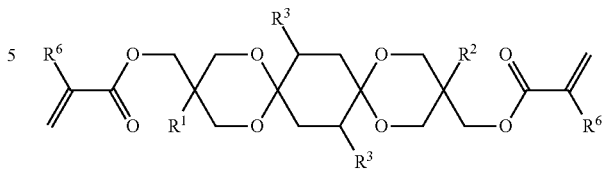

(4)

in the formula (4), each of $R^1$ and $R^2$ independently represents a hydrocarbon group; each $R^3$ independently represents a hydrogen atom, hetero atom-containing group, halogen atom, straight chain alkyl group having 1 to 6 carbon atoms, branched alkyl group having 3 to 6 carbon atoms or, aryl group-containing group having 6 to 12 carbon atoms; and each $R^6$ independently represents a hydrogen atom or methyl group.

One example of the hydrocarbon group in the embodiment is straight chain alkyl group having 1 to 7 carbon atoms, branched alkyl group having 3 to 7 carbon atoms or aryl group, and another example is straight chain alkyl group having 1 to 7 carbon atoms or branched alkyl group having 3 to 7 carbon atoms.

$R^1$ and $R^2$ in the formula (4) are synonymous to $R^1$ and $R^2$ in the formula (1), along with the same preferred ranges.

Each $R^3$ in the formula (4) is synonymous to $R^3$ in the formula (1), along with the same preferred ranges.

Each $R^6$ in the formula (4) preferably represents a hydrogen atom.

The di(meth)acrylate in this embodiment is synthesized by a dehydration condensation reaction between the diol represented by the formula (1) of the embodiment, and (meth)acrylic acid; or by a transesterification reaction between the diol represented by the formula (1) in this embodiment, and a (meth)acrylate. The (meth)acrylic acid is preferably acrylic acid, and the (meth)acrylate is preferably an acrylate.

In the dehydration condensation reaction, it is preferable to use 2 to 10 mol, more preferably 2.5 to 5 mol, of (meth)acrylic acid per one mole of polyol. In the transesterification reaction, it is preferable to use 2 to 20 mol, more preferably 2.5 to 8 mol, of (meth)acrylate per one mole of polyol.

The dehydration condensation reaction between the diol represented by the formula (1) and (meth)acrylic acid may be allowed to proceed by any of known methods, using an acid catalyst, organic solvent and polymerization inhibitor.

The acid catalyst employable for the dehydration condensation reaction may freely be selected from known substances including sulfuric acid, hydrochloric acid, phosphoric acid, methanesulfonic acid, para-toluenesulfonic acid, benzenesulfonic acid, boron trifluoride, and cationic ion exchange resin.

Two or more catalysts may be used at the same time. The amount to be used of catalyst is preferably 0.1 to 10 mol % per one mole of diol, and is more preferably 1 to 5 mol %.

Although the organic solvent is not specifically limited so long as it does not cause side reaction with the starting material, preferable are those capable of removing the produced water out of the system in order to accelerate the reaction, that is, those capable of staying separated from the water phase, and can distill azeotropically with water. Preferably employable are organic solvents selected, for example, from hexane, heptane, cyclohexane, methylcyclohexane, benzene, toluene and xylene. Two or more organic solvents may be used in a combined manner. As for the amount to be used of organic solvent, minimum requirement of the organic solvent necessary for azeotropic removal of water may be derived based on the theoretical amount of produced water, and ratio of azeotropic composition of water and organic solvent. It is even possible to reduce the amount of consumption below the theoretical value, by using a Dean-Stark apparatus which can remove water while continuously returning an azeotropic organic solvent into a reaction vessel. More simply, the amount of organic solvent is preferably 20 to 200% by mass of the total mass of the diol represented by the formula (1) and (meth)acrylic acid, which is more preferably 30 to 100% by mass.

The polymerization inhibitor is not specifically limited so long as it can scavenge radicals, and is freely selectable from known substances such as hydroquinone, para-methoxyphenol, tert-butylhydroquinone, para-benzoquinone and 2,2,6,6-tetramethylpiperidine-1-oxide.

Two or more polymerization inhibitors may be used at the same time. The amount to be used of polymerization inhibitor is preferably 0.001 to 5% by mass of (meth)acrylic acid, and is more preferably 0.01 to 1% by mass.

The transesterification reaction between the diol represented by the formula (1) and (meth)acrylate may be allowed to proceed by any of known methods, using a catalyst (Lewis acid catalyst or base catalyst, preferably Lewis acid catalyst), and a polymerization inhibitor.

As the (meth)acrylate, employable are any of known (meth)acrylates including methyl (meth)acrylate, ethyl (meth)acrylate, n-propyl (meth)acrylate, isopropyl (meth)acrylate, and n-butyl (meth)acrylate. In particular, considering easy removal of produced alcohols by distillation, the (meth)acrylate used for the transesterification reaction is preferably methyl (meth)acrylate. Only one (meth)acrylate may be used, or two or more of them may be used.

Since the reaction can proceed rapidly by removing lower alcohols produced in the reaction out from the system, so that it is preferable to use a reactor equipped with a distillation column, and to allow the reaction to proceed while removing the lower alcohols.

Any of known Lewis acid catalysts are employable for the transesterification reaction, which are selected for example from dimethyltin oxide, dibutyltin oxide, dimethyltin dichloride, dibutyltin dichloride, aluminum isopropoxide, zinc acetylacetonate, tetramethoxytitanium, tetraisopropoxytitanium and tetrabutoxytitanium. Alternatively, these Lewis acid catalysts may be generated in the reaction system, by using a base.

Meanwhile, the transesterification reaction can also employ any of known bases, such as lithium methoxide, sodium methoxide, potassium methoxide, lithium ethoxide, sodium ethoxide and potassium ethoxide.

Two or more catalysts may be used at the same time, properly so long as they will not cause problems.

The polymerization inhibitor preferably employable is the polymerization inhibitor having been described regarding the dehydration condensation reaction between the diol represented by the formula (1) and (meth)acrylic acid.

The di(meth)acrylate in the embodiment, represented by the formula (4), may be used as a reactive diluent or viscosity modifier, typically applicable to paint, coating material, hard coating material, ink, adhesive, pressure sensitive adhesive, resist material, molding material, and surface finishing agent.

EXAMPLES

This invention will further be detailed referring to Examples. This invention is, however, not specifically limited by Examples below. All notation in "%" is based on mass, unless otherwise specifically noted.

Analytical methods for physical properties, employed in Examples, are as follows.
(1) Reaction Yield and Purity of Product The reaction yield and the purity of product were quantified by gas chromatography (apparatus: Agilent 6850, from Agilent Technologies, Inc.) or high performance liquid chromatography (apparatus: Chromaster, from Hitachi High-Tech Science Corporation), based on the internal standard method.
(2) Nuclear Magnetic Resonance (NMR)

NMR (Model: JNM-ECA500, from JEOL Ltd.) was employed for structural determination of compounds. Employed deuterated solvent and measurement frequency will be denoted in assignment data of the individual compounds.
(3) High Resolution Mass Spectrometry High resolution mass spectrometry (HR-MS, MS) of compounds was carried out by the direct injection method for LC-MS, or DART (Direct Analysis in Real Time) method.

HPLC (High-performance liquid chromatography) apparatus: U3000 (from Thermo Fisher Scientific Inc.)

DART apparatus: DART-Os (from AMR Inc.)

MS apparatus: LTQ Orbitrap Discovery (from Thermo Fisher Scientific Inc.)

Measurement Conditions for HPLC
  Column: not used
  Mobile phase: mixed solution of 0.1% by mass aqueous formic acid solution and acetonitrile (50:50, v/v)
  Flow rate: 0.2 mL/min
  Sample concentration: 100 ppm by mass
  Injection volume: 10 μL Measurement Conditions for MS (Under LC-MS Direct Injection)
  Ionization method: Positive ESI
  Capillary temperature: 300° C.
  Capillary voltage: 22 V
  Tube lens voltage: 100 V Measurement Conditions for DART
  Ion source temperature: 400° C.

Measurement Conditions for MS (Under DART)
  Ionization method: DART
  Capillary temperature: 200° C.
  Capillary voltage: 35 V
  Tube lens voltage: 100 V (4) Melting Point Melting points of the compounds were measured by using a differential scanning calorimeter (Model: DSC7020, from Hitachi High-Tech Science Corporation), placing approximately 10 mg of a sample into an aluminum non-hermetic container made of aluminum, under nitrogen gas flow, at a rate of temperature rise of 10° C./min.
(5) Measurement of Heat Resistance Heat resistance of the compounds was measured using Thermo Plus TG8120 from Rigaku Corporation. The compounds were heated up to 190° C. at a rate of temperature rise of 10° C./min under a rate of nitrogen gas flow of 150 mL/min, and weight loss was measured at a constant temperature of 190° C.

Example 1

In a 300 mL round-bottom flask, placed were 10.0 g of 1,4-cyclohexanedione (from Tokyo Chemical Industry Co., Ltd., reagent), 25.1 g of trimethylolpropane (from Mitsubishi Gas Chemical Company, Inc.), 300 g of toluene (from Wako Pure Chemical Industries, Ltd., special grade reagent), and 0.26 g of methanesulfonic acid (from Tokyo Chemical Industry Co., Ltd., reagent), and the content was heated under normal pressure so as to control the temperature inside vessel within the range from 90° C. to 112° C., allowing a dehydration cyclization reaction to proceed. At this temperature, the reaction was allowed to continue while removing the water in the system resulted from the reaction, azeotropically with toluene through a Dean-Stark trap out from the system, for 10 hours until distillation of water came to the end. In the reaction system after removal of water, the product was found to form a slurry. The reaction slurry was cooled down to 25° C., filtered, washed with aqueous sodium hydroxide solution for neutralization, washed with water, and dried under reduced pressure, to obtain 30.3 g of Compound A (purity (determined by GC)=98.4%, isolation yield=97%).

A reaction scheme of Example 1 is shown below.

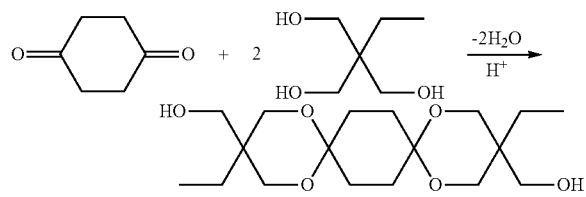

Structure of Compound A obtained in Example 1 was determined by $^1$HNMR, $^{13}$CNMR, DEPT, H—H COSY and HMQC spectra.

$^1$H NMR (500 MHz, DMSO-d6) δ 0.74 (3H x 2, t, CH$_3$CH$_2$— x 2), 1.24 (2H x 2, q, CH$_3$CH$_2$— x 2), 1.56-1.63 & 1.73-1.81 (4H x 2, m, cyclohexane), 3.40 (2H x 2, d, CH$_2$OH x 2), 3.48, 3.57 (4H x 2, 2d, —CH$_2$—O—C— x 4), 4.52 (1H x 2, t, OH x2), $^{13}$C NMR (125 MHz, DMSO-d6) δ 6.84, 22.9, 25.7, 30.4, 36.4, 60.2, 63.8, 96.8.

Peaks at δ25.7 and 30.4 in $^{13}$C NMR were assigned to four methylene groups on the cyclohexane ring, observed by twos as being non-equivalent, referring to DEPT135 and HMQC spectra.

Compound A was further measured regarding molecular weight by LC-MS analysis (electrospray method [ESI positive mode] and high resolution mass spectrometry (HR-MS)). Since mass spectrometry based on the electrospray method can ionize a molecule almost without causing fragmentation, so that information on its molecular weight is obtainable. When combined with high-resolution mass spectrometry, the molecules can be examined to identify its compositional formula. Since the mass number (molecular weight M plus one) of the protonated molecule [M+H]$^+$, keeping the intact structure, was observed to be 345.22620 (C$_{18}$H$_{33}$O$_6$), the compositional formula of Compound A was determined as C$_{18}$H$_{32}$O$_6$.

Example 2

The dehydration cyclization reaction was allowed to proceed under the same conditions as in Example 1, except that 25.1 g trimethylolpropane was replaced with 22.5 g of trimethylolethane (from Mitsubishi Gas Chemical Company, Inc.), at a temperature inside vessel of 95° C. to 112. Compound B obtained after dried under reduced pressure was found to amount to 27.1 g (purity (determined by GC)=98.2%, isolation yield=94%).

A reaction scheme of Example 2 is shown below.

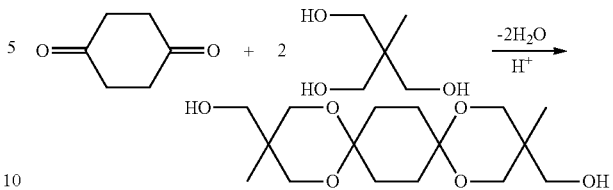

Structure of Compound B obtained in Example 2 was determined by $^1$HNMR, $^{13}$CNMR, DEPT, H—H COSY and HMQC spectra.

$^1$H NMR (500 MHz, DMSO-d6) δ 0.75, 0.76 (3H x 2, s x 2, CH$_3$— x 2), 1.56-1.63 & 1.73-1.81 (4H x 2, m, cyclohexane), 3.35 (2H x 2, d, CH$_2$OH x 2), 3.44, 3.57 (4H x 2, 2d, —CH$_2$—O—C— x 4), 3.62 (1H x 2, bs, OH x2); $^{13}$C NMR (125 MHz, DMSO-d6) δ 17.7, 25.8, 30.3, 34.6, 63.8, 65.1, 96.8.

Peaks at δ25.8 and 30.3 in $^{13}$C NMR were assigned to four methylene groups on the cyclohexane ring, observed by twos as being non-equivalent, referring to DEPT135 and HMQC spectra.

Compound B was further measured regarding molecular weight by LC-MS analysis. Since the mass number (molecular weight M plus one) of the protonated molecule [M+H]$^+$, keeping the intact structure, was observed to be 317.19489 (C$_{16}$H$_{29}$O$_6$), the compositional formula of Compound B was determined as C$_{16}$H$_{28}$O$_6$.

Example 3

The dehydration cyclization reaction was allowed to proceed under the same conditions as in Example 1, except that 0.26 g of methanesulfonic acid was replaced with 0.51 g of para-toluenesulfonic acid monohydride (from Wako Pure Chemical Industries, Ltd., special grade reagent). Compound A obtained after dried under reduced pressure was found to amount to 30.9 g (purity (determined by GC)=97.5%, isolation yield=98%).

Example 4

The dehydration cyclization reaction was allowed to proceed under the same conditions as in Example 1, except that 300 g of toluene was replaced with 300 g of cyclohexane (from Wako Pure Chemical Industries, Ltd., special grade reagent). Compound A obtained after dried under reduced pressure was found to amount to 31.0 g (purity (determined by GC)=96.5%, isolation yield=97%).

Example 5

The dehydration cyclization reaction was allowed to proceed under the same conditions as in Example 1, except that 25.1 g of trimethylolpropane was replaced with 12.5 g of trimethylolpropane (from Mitsubishi Gas Chemical Company, Inc.) and 11.2 g of trimethylolethane (from Mitsubishi Gas Chemical Company, Inc.), at a temperature inside vessel of 95° C. to 112. A product obtained after dried under reduced pressure was found to be a mixture of Compound A, Compound B and Compound C, amounting to 28.4 g (purity (determined by GC)=96.5%, Compound A:Compound B:Compound C=44:7:49, isolation yield=969, calculated solely as Compound C).

A reaction scheme of Example 5 is shown below.

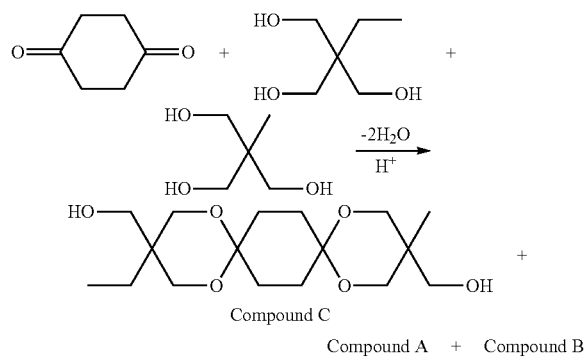

Compound C obtained in Example 5 was identified by measuring HR-MS in DART-MS analysis. Since the mass number (molecular weight M plus one) of the protonated molecule $[M+H]^+$ was observed to be 331.21131 ($C_{17}H_{31}O_6$), the compositional formula of Compound C was determined as $C_{17}H_{30}O_6$.

Melting points of Compound A obtained in Example 1, Compound B obtained in Example 2, and the Compound C-containing mixture obtained in Example 5 were measured by DSC. Also melting points of spiroglycol (from Mitsubishi Gas Chemical Company, Inc.) as Comparative Example 1, isosorbide (from Tokyo Chemical Industry Co., Ltd., purity≥98%) as Reference Example 1, and cyclohexanediol (from Tokyo Chemical Industry Co., Ltd., cis-trans mixture, purity≥99%) as Reference Example 2 were measured. Results of measurement are shown in Table 1 below.

TABLE 1

|  | Example 1 | Example 2 | Example 5 | Comparative Example 1 | Reference Example 1 | Reference Example 2 |
| --- | --- | --- | --- | --- | --- | --- |
| Name | Compound A | Compound B *1 | Mixture Containing Compound C | Spiroglycol | Isosorbide | Cyclohexane diol |
| Melting Point (DSC) | 177° C. | 181, 197, 218° C. | 120, 161, 218° C. | 205° C. | 54° C. | 105° C. |

*1 Compounds B and C showed a plurality of melting points attributable to differences in steric structure.

It was understood from the results in Table 1 that the diols represented by the formula (1), obtainable in the embodiments, tend to have melting points lower than that of spiroglycol having an analogous spiro structure.

Heat resistance of Compound A obtained in Example 1, Compound B obtained in Example 2, and Compound C-containing mixture obtained in Example 5 was evaluated according to the method described above. Also heat resistance of spiroglycol (from Mitsubishi Gas Chemical Company, Inc.) as Comparative Example 1 was evaluated. Weight loss of the individual Compounds after 240 minutes are summarized in Table 2.

TABLE 2

|  | Example 1 | Example 2 | Example 5 | Comparative Example 1 |
| --- | --- | --- | --- | --- |
| Name | Compound A | Compound B | Mixture Containing Compound C *1 | Spiroglycol |
| Rate of Weight Loss | −44.2% | −42.6% | −43.5% | −98.7% |

*1 Compound A:Compound B:Compound C = 44:7:49

It was found from the results in Table 2 that, while spiroglycol almost disappeared after being kept constant at 190° C. for 240 minutes, the diol represented by the formula (1), obtainable in the embodiment, was found to retain approximately 50% of the mass thereof, proving a distinctively higher heat resistance over spiroglycol.

Example 6

To 17.2 g of Compound A obtained in Example 1, added were 13.1 g of acrylic acid (from Wako Pure Chemical Industries, Ltd., special grade reagent), 0.54 g of para-toluenesulfonic acid (from Wako Pure Chemical Industries, Ltd., special grade reagent), 59.7 mg of hydroquinone (from Wako Pure Chemical Industries, Ltd., special grade reagent), 80.6 mg of para-methoxyphenol (from Wako Pure Chemical Industries, Ltd., special grade reagent), 19.9 g of toluene (from Wako Pure Chemical Industries, Ltd., special grade reagent), and 19.9 g cyclohexane (from Wako Pure Chemical Industries, Ltd; special grade reagent), and the mixture was allowed react on an oil bath at 96° C. for 13 hours, while removing the distilled water. After cooled down to room temperature, the content was washed four times using 15 mL each of a 20% by mass aqueous sodium hydroxide solution, and then washed three times using 15 mL each of water. After adding 16 mg of para-methoxyphenol, the content was condensed using an evaporator, and the obtained solid was thoroughly washed using an 8:1 (v/v) hexane/ethyl acetate mixed solution, to obtain crystalline Compound D.

A reaction scheme of Example 5 is shown below.

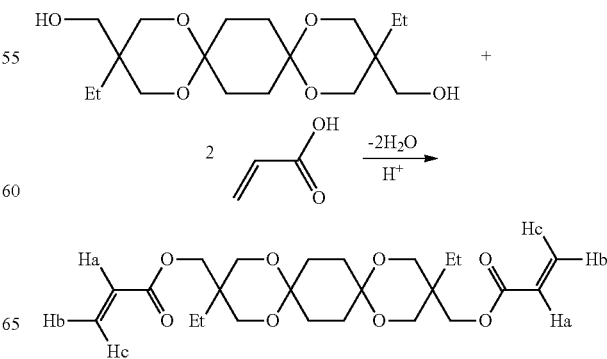

Structure of Compound D obtained in Example 6 was determined by $^1$HNMR, $^{13}$CNMR, DEPT and HMQC spectra.

$^1$H NMR (500 MHz, CDCl$_3$) δ 0.83 (3H x 2, t, CH$_3$CH$_2$— x 2), 1.32 (2H x 2, q, CH$_3$CH$_2$— x 2), 1.68-1.74 & 1.93-1.97 (4H x 2, m, cyclohexane), 3.66 3.69 (4H x 2, 2d, —CH$_2$—O—C— x 4), 4.31 (2H x 2, s, —CH$_2$O—C(O)— x 2), 5.84 (1H x 2, dd, Hb x 2), 6.13 (1H x 2, dd, Ha x2), 6.39 (1H x 2, dd, Hc x 2); $^{13}$C NMR (125 MHz, CDCl$_3$)δ 6.88, 24.0, 24.5, 31.9, 36.0, 64.0, 64.6, 97.8, 128.3, 130.7, 166.1.

Peaks at δ24.5 and 31.9 in $^{13}$C NMR were assigned to four methylene groups on the cyclohexane ring, observed by twos as being non-equivalent, referring to DEPT135 and HMQC spectra.

Melting point of Compound D obtained in Example 6 was measured by DSC. Also melting points of spiroglycol diacrylate (compound described in JP-A-S63-268722) as Comparative Example 2, isosorbide diacrylate (compound described in GB-A-586141) as Reference Example 3, trans-cyclohexane dimethanol diacrylate (compound described in *Journal of Polymer Science Part A*-1: Polymer Chemistry (1966), 4, 519-28) as Reference Example 4, and tricyclodecane dimethanol diacrylate (from Sigma-Aldrich Inc.) as Reference Example 5, are shown below.

TABLE 3

|  | Example 6 | Comparative Example 2 | Reference Example 3 | Reference Example 4 | Reference Example 5 |
|---|---|---|---|---|---|
| Name | Compound D | Spiro Glycol Diacrylate | Isosorbide Diacrylate | Cyclohexane Dimethanol Diacrylate | Tricylododecane Dimethanol Diaccylate |
| Melting Point (DSC) | 147° C. | 105 to 125° C. | 57° C. | 81° C. | 10° C. or less |

It was found from the results in Table 3 that diacrylate of this invention has a melting point higher than that of spiroglycol diacrylate having an analogous alicyclic structure.

Example 7

In a 300 mL round-bottom flask, placed were 1.47 g of 1,4-cyclohexanedione (from Tokyo Chemical Industry Co., Ltd., reagent), 5.0 g of α,α,α-tris(hydroxymethyl) toluene (from Toronto Research Chemicals), 100 g of toluene (from Wako Pure Chemical Industries, Ltd., special grade reagent), and 0.08 g of para-toluenesulfonic acid monohydrate (from Wako Pure Chemical Industries, Ltd., special grade reagent), and the content was heated under normal pressure so as to control the temperature inside vessel within the range from 90° C. to 112° C., allowing a dehydration cyclization reaction to proceed. At this temperature, the reaction was allowed to continue while removing the water in the system resulted from the reaction, azeotropically with toluene through a Dean-Stark trap out from the system, for 4 hours until distillation of water came to the end. In the reaction system after removal of water, the product was found to form a slurry. The reaction slurry was cooled down to 25° C., filtered, washed with aqueous sodium hydroxide solution for neutralization, washed with water, and dried under reduced pressure, to obtain 5.0 g of Compound E (purity (determined by HPLC)=98.5%, isolation yield=86%).

A reaction scheme of Example 7 is shown below.

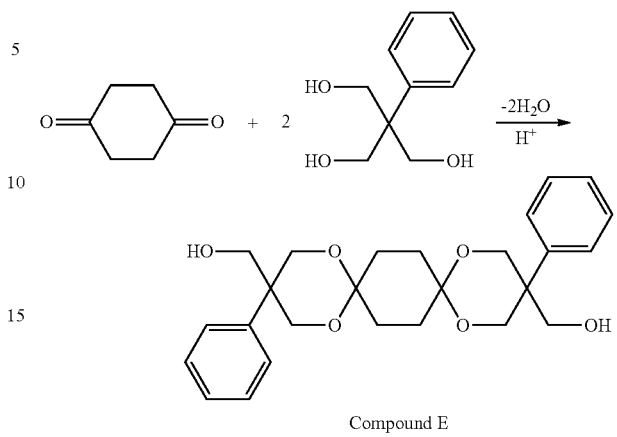

Compound E

Structure of Compound E obtained in Example 7 was determined by $^1$HNMR, $^{13}$CNMR, DEPT, H—H COSY and HMQC spectra.

$^1$H NMR (500 MHz, DMSO-d6) δ 0.74 (3H x 2, t, CH$_3$CH$_2$— x 2), 1.24 (2H x 2, q, CH$_3$CH$_2$— x 2), 1.62-1.70 & 1.81-1.91 (4H x 2, m, cyclohexane), 3.77 (2H x 2, s, CH$_2$OH x 2), 3.96, 4.06 (4H x 2, 2d, —CH$_2$—O—C— x 2), 7.19-7.24 (1H x 2, m, Ph), 7.27-7.34 (4H x 2, m, Ph); $^{13}$C NMR (125 MHz, DMSO-d6) δ25.1, 31.3, 41.2, 63.3, 63.6, 96.9, 126.2, 126.5, 128.0, 142.0.

Peaks at δ25.1 and 31.3 in $^{13}$CNMR were assigned to four methylene groups on the cyclohexane ring, observed by twos as being non-equivalent, referring to DEPT135 and HMQC spectra.

Compound E obtained in Example 7 was identified by measuring HR-MS in DART-MS analysis. Since the mass number (molecular weight M plus one) of the protonated molecule [M+H]$^+$ was observed to be 441.22717 (C$_{26}$H$_{33}$O$_6$), the compositional formula of Compound E was determined as C$_{26}$H$_{32}$O$_6$.

ADVANTAGEOUS EFFECTS OF INVENTION

The diol having a dispiro structure, obtainable by the embodiment, surpasses spiroglycol in thermal stability, tends to have lower melting point, and has improved handleability. Hence in manufacture of various resins (thermoplastic resins) using the diol component as the starting material, production efficiency and workability will be expected to be improved. Since the diol is a monomer with a rigid structure, the obtainable various resins (thermoplastic resin) are expected to have improved physical properties (high hardness, friction resistance, transparency, heat resistance, weatherability, optical characteristics). This invention can therefore enjoy a large industrial availability.

The invention claimed is:

1. A diol represented by the following formula (1):

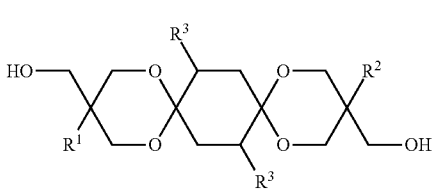

(1)

wherein each of $R^1$ and $R^2$ independently represents a hydrocarbon group having 1 to 7 carbon atoms; and each $R^3$ independently represents a hydrogen atom, a group having at least one of an oxygen atom, a sulfur atom, and a nitrogen atom, a halogen atom, a straight chain alkyl group having 1 to 6 carbon atoms, a branched alkyl group having 3 to 6 carbon atoms, or an aryl group-containing group having 6 to 12 carbon atoms.

2. The diol of claim 1, wherein each $R^3$ in the formula (1) independently represents a hydrogen atom, a straight chain alkyl group having 1 to 6 carbon atoms, a branched alkyl group having 3 to 6 carbon atoms, or an aryl group-containing group having 6 to 12 carbon atoms.

3. The diol of claim 1, wherein each $R^3$ in the formula (1) independently represents a hydrogen atom or a methyl group.

4. The diol of claim 1, wherein each of $R^1$ and $R^2$ in the formula (1) independently represents a straight chain alkyl group having 1 to 7 carbon atoms, a branched alkyl group having 3 to 7 carbon atoms or an aryl group.

5. The diol of claim 1, wherein each of $R^1$ and $R^2$ in the formula (1) independently represents a straight chain alkyl group having 1 to 7 carbon atoms or a branched alkyl group having 3 to 7 carbon atoms.

6. The diol of claim 1, wherein each of $R^1$ and $R^2$ in the formula (1) independently represents a straight chain alkyl group having 1 to 7 carbon atoms or an aryl group.

7. The diol of claim 1, wherein each of $R^1$ and $R^2$ in the formula (1) independently represents an ethyl group, a methyl group or a phenyl group, and each $R^3$ represents a hydrogen atom.

8. A method for manufacturing the diol of claim 1, the method comprising:
reacting a 1,4-cyclohexanedione derivative represented by the following formula (2) with a triol represented by the following formula (3) to undergo a dehydration cyclization reaction:

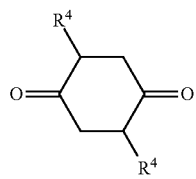

(2)

wherein each $R^4$ represents a hydrogen atom, a group having at least one of an oxygen atom, a sulfur atom, and a nitrogen atom, a halogen atom, a straight chain alkyl group having 1 to 6 carbon atoms, a branched alkyl group having 3 to 6 carbon atoms, or an aryl group-containing group having 6 to 12 carbon atoms;

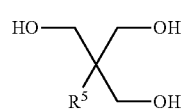

(3)

wherein $R^5$ represents a hydrocarbon group having 1 to 7 carbon atoms.

9. The method of claim 8, wherein, in the formula (3), $R^5$ represents a straight chain alkyl group having 1 to 7 carbon atoms, a branched alkyl group having 3 to 7 carbon atoms or an aryl group.

10. The method of claim 8, wherein, in the formula (3), $R^5$ represents a straight chain alkyl group having 1 to 7 carbon atoms or a branched alkyl group having 3 to 7 carbon atoms.

11. The method of claim 8, wherein the dehydration cyclization reaction is performed in the presence of an acid catalyst.

12. The method of claim 11, wherein the acid catalyst comprises at least one selected from the group consisting of methanesulfonic acid and para-toluenesulfonic acid.

13. The method according to claim 8, the method further comprising removing water resulting from the dehydration cyclization reaction, out from the reaction system.

14. The method of claim 13, wherein the water resulting from the dehydration cyclization reaction is removed azeotropically with an organic solvent.

15. The method of claim 14, wherein the organic solvent comprises at least one selected from the group consisting of toluene and cyclohexane.

16. The method of claim 8, wherein the compound represented by the formula (2) is 1,4-cyclohexanedione, and the compound represented by the formula (3) is at least one selected from the group consisting of trimethylolpropane, trimethylolethane and tris(hydroxymethyl)toluene.

17. The method of claim 8, wherein the compound represented by the formula (2) is 1,4-cyclohexanedione, and the compound represented by the formula (3) is at least one selected from the group consisting of trimethylolpropane and trimethylolethane.

18. A di(meth)acrylate represented by the following formula (4):

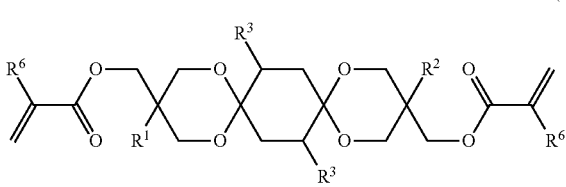

(4)

wherein each of $R^1$ and $R^2$ independently represents a hydrocarbon group having 1 to 7 carbon atoms, each $R^3$ independently represents a hydrogen atom, a group having at least one of an oxygen atom, a sulfur atom, and a nitrogen atom, a halogen atom, a straight chain alkyl group having 1 to 6 carbon atoms, a branched alkyl group having 3 to 6 carbon atoms, or an aryl group-containing group having 6 to 12 carbon atoms, and each $R^6$ independently represents a hydrogen atom or a methyl group.

19. The di(meth)acrylate of claim 18, wherein each $R^3$ in the formula (4) independently represents a hydrogen atom, a straight chain alkyl group having 1 to 6 carbon atoms, a branched alkyl group having 3 to 6 carbon atoms or an aryl group-containing group having 6 to 12 carbon atoms.

20. The di(meth)acrylate of claim 18, wherein each $R^3$ in the formula (4) independently represents a hydrogen atom or a methyl group.

21. The di(meth)acrylate of claim 18, wherein each of $^1$ and $R^2$ in the formula (4) independently represents a straight chain alkyl group having 1 to 7 carbon atoms, a branched alkyl group having 3 to 7 carbon atoms or an aryl group.

22. The di(meth)acrylate of claim 18, wherein each of $R^1$ and $R^2$ in the formula (4) independently represents a straight chain alkyl group having 1 to 7 carbon atoms or a branched alkyl group having 3 to 7 carbon atoms.

23. The di(meth)acrylate of claim 18, wherein each of $R^1$ and $R^2$ in the formula (4) independently represents a straight chain alkyl group having 1 to 7 carbon atoms or an aryl group.

24. The di(meth)acrylate of claim 18, wherein each of $^1$ and $R^2$ in the formula (4) independently represents an ethyl group, methyl group or phenyl group; and each $R^3$ represents a hydrogen atom.

25. A method for manufacturing a di(meth)acrylate, the method comprising reacting the diol according to claim 1 with (meth)acrylic acid to undergo a dehydration condensation reaction.

* * * * *